Figure 1:
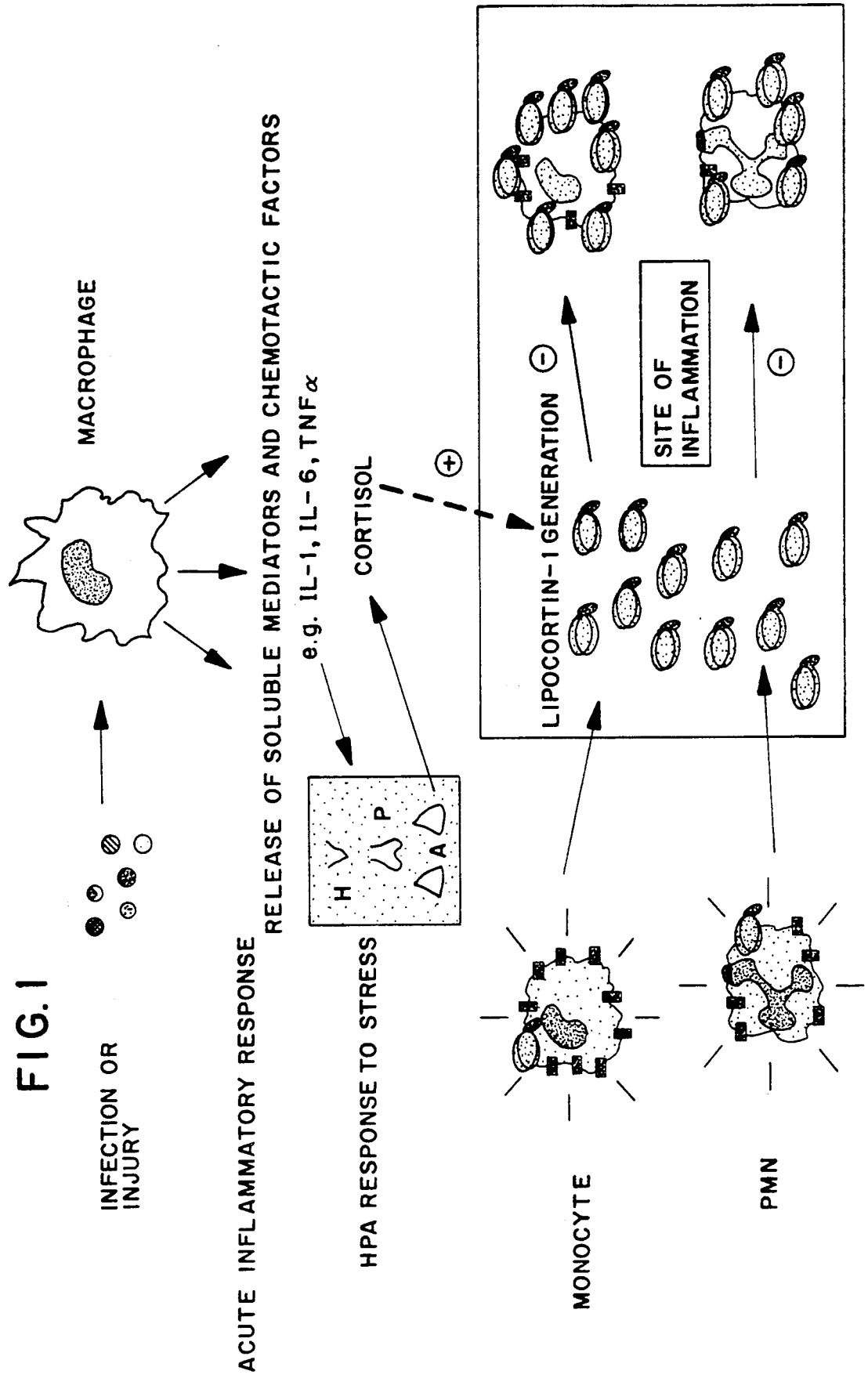

United States Patent [19]

Guyre et al.

[11] Patent Number: 5,314,992
[45] Date of Patent: May 24, 1994

[54] LIPOCORTIN-1 RECEPTOR PROTEIN AND ITS USES

[75] Inventors: Paul M. Guyre, Hanover, N.H.; Nicolas J. Goulding, Bath, England

[73] Assignee: Trustees of Dartmouth College, Hanover, N.H.

[21] Appl. No.: 797,330

[22] Filed: Nov. 25, 1991

[51] Int. Cl.$^5$ ............................................. C07K 15/00
[52] U.S. Cl. ...................................... 530/350; 530/395
[58] Field of Search ...................... 530/350, 827, 388.1, 530/388.2, 829, 395; 536/27, 23.1; 435/69.1, 172.3, 240.2, 252.3, 7.1, 69.1

[56] References Cited

U.S. PATENT DOCUMENTS

| | | | |
|---|---|---|---|
| 4,874,743 | 10/1989 | Wallner et al. | 514/12 |
| 4,879,224 | 11/1989 | Wallner et al. | 435/68 |
| 4,917,826 | 4/1990 | Johnson et al. | 552/522 |
| 4,937,324 | 6/1990 | Fujikawa et al. | 530/397 |
| 4,950,646 | 8/1990 | Wallner et al. | 514/12 |
| 5,051,364 | 9/1991 | Isacke et al. | 435/240.27 |

FOREIGN PATENT DOCUMENTS

| | | |
|---|---|---|
| 0330396 | 6/1986 | European Pat. Off. |
| WO9109953 | 7/1991 | PCT Int'l Appl. |

OTHER PUBLICATIONS

Jacobs, et al., "Isolation and Characterization of Genomic and cDNA Clones of Human erythropoietin", Nature, vol. 313, Feb. 28, 1985, pp. 806–810.

Ando et al., "Calcium-induced Intracellular Cross--linking of Lipocortin I by Tissue Transglutaminase in A431 Cells", The Journal of Biological Chemistry, 1991, vol. 266, No. 2, pp. 1101–1108.

Ando et al., "Enhancement of Calcium Sensitivity of Lipocortin I in Phospholipid Binding Induced by Limited Proteolysis and Phosphorylation at the Amino Terminus as Analyzed by Phospholipid Affinity Column Chromatography", The Journal of Biological Chemistry, 1989, vol. 264, No. 12, pp. 6948–6955.

Andree et al., "Binding of Vascular Anticoagulant (VAC) to Planar Phospholipid Bilayers", The Journal of Biological Chemistry, 1990, vol. 265, No. 9, pp. 4923–4928.

Blackwood et al., "Characterization of $Ca^{2+}$-dependent Phospholipid Binding, vesicle Aggregation and Membrane Fusion by annexins", Biochem. J., 1990, vol. 266, pp. 195–200.

Meers "Location of Tryptophans in Membrane-Bound Annexins", Biochemistry, 1990, vol. 29, No. 13, pp. 3325–3330.

Tait et al., "Phospholipid Binding Properties of Human Placental Anticoagulant Protein-I, a Member of the Lipocortin Family", The Journal of Biological Chemistry, 1989, vol. 264, No. 14, pp. 7944–7949.

Thomas et al., 1990, Methods in Enzymology, 182, 499–520, "Purification of Membrane Proteins".

Goulding et al., Characteristics of Lipocortin-I Binding . . . , 1990, Biochem. Soc. Trans., 18(6), 1237–8.

Hirata et al., (1980), Biochem., 77:1553–2536.

Wallner et al., (1986), Nature, 320:77–81.

Flower, (1988), Br. J. Pharmacol., 94:987–1015.

Fradin et al., (1988), Biochim. Biophys. Acta, 963:248–257.

Glenney et al., (1988), Biochem., 27:2069–2076.

Pepinsky et al., (1988), J. Biol. Chem., 263:10799–10811.

Cirino et al., (1989), Proc. Natl. Acad. Sci. USA, 86:3428–3432.

Maridonneau-Parini et al., (1989), J. Clin. Invest., 83:1936–1940.

Rothhut et al., (1989), Biochem. J., 263:929–935.

Browing et al., (1990), in Cytokines and Lipocortins-I in Inflammation and Differentiation, (Melli et al., eds.), Wiley-Liss, New York, pp. 27–45.

Goulding et al., (1990), Lancet, 335:1416–1418.

*Primary Examiner*—Robert J. Hill, Jr.
*Assistant Examiner*—Sally Teng
*Attorney, Agent, or Firm*—Lahive & Cockfield

[57] ABSTRACT

A new cellular protein produced by activated monocytes/neutrophils and mononuclear cells, and involved in the binding of lipocortin-1 has been discovered. Methods for isolating and purifying this substantially pure lipocortin-1 receptor protein are disclosed herein as well as techniques for cloning and expressing the protein and related materials. Techniques for raising monoclonal antibodies to this protein, and diagnostic and therapeutic uses for this protein are also disclosed.

4 Claims, 5 Drawing Sheets

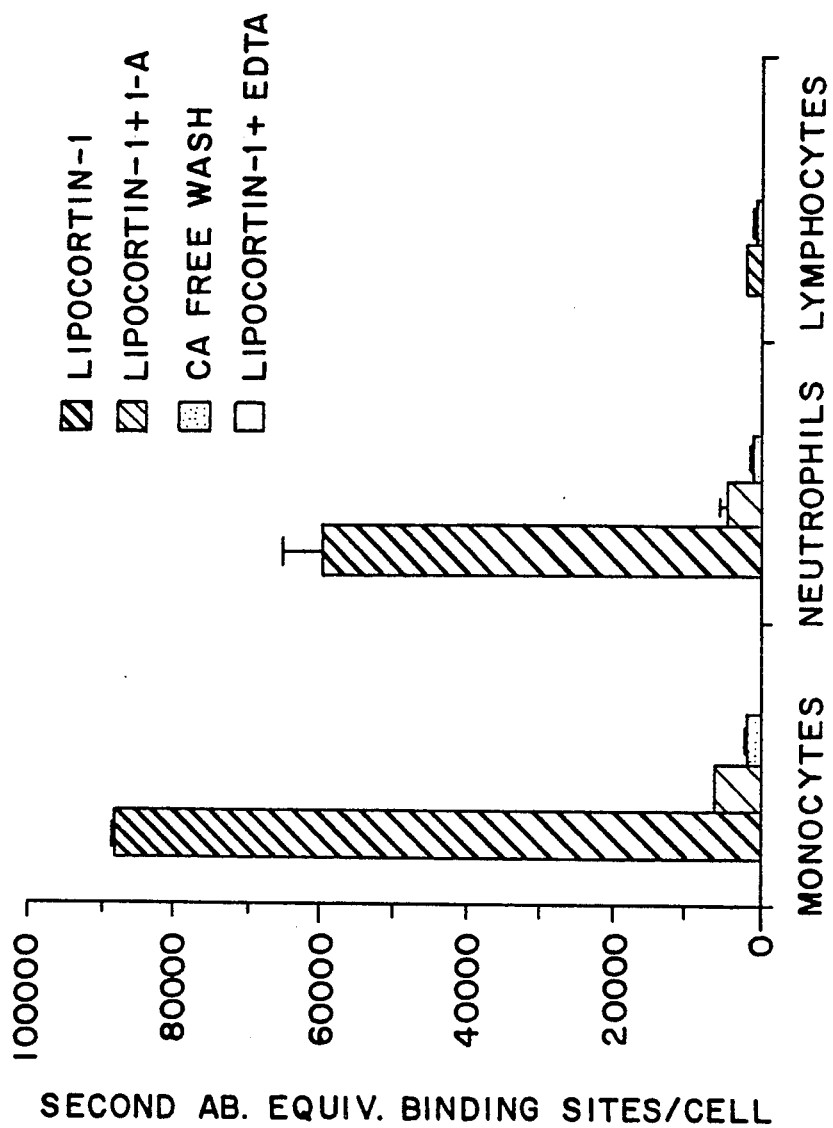

5,314,992

LIPOCORTIN-1 RECEPTOR PROTEIN AND ITS USES

GOVERNMENT SUPPORT

The work leading to this invention is supported by one or more grants from the U.S. Government.

BACKGROUND OF THE INVENTION

Lipocortins (also termed "annexins") are a family of widely distributed calcium-binding proteins which have been studied in diverse biological systems, mainly with regard to their interactions with phospholipids and membranes, their potential role in membrane aggregation and regulation of cell growth and differentiation (Blackwood et al. (1990) *Biochem J.* 266:195-200; Burgoyne et al. (1989) *Cell Calcium* 10:1-10; Klee (1988) *Biochem.* 27:6645-6653). The lipocortins have also been implicated in inhibition of phospholipase $A_2$ ($PLA_2$) activity (Flower (1988) *Br. J. Pharmacol.* 94:987-1015). Phospholipase $A_2$ is responsible for the release of arachidonic acid from membrane phospholipids. Arachidonic acid is a precursor in the synthesis of a number of compounds (e.g., prostaglandins, hydroxy-acids and leukotines) involved in the inflammation process. Accordingly, lipocortins are believed to inhibit inflammation by inhibiting the synthesis of inflammation-inducing substances.

Certain members of the lipocortin family have been shown to be generated in response to anti-inflammatory agents such as glucocorticoids (Smillie et al. (1990) *Br. J. Pharmacol.* 97:425P; Goulding et al. (1990) *Lancet* 335:1416-1418). A multiplicity of functions have been ascribed to the various annexins, including mediation of some of the anti-inflammatory effects of glucocorticoids in animal models (Cirino et al. (1989) *Proc. Natl. Acad. Sci. (USA)* 86:3428-3432; Errasfa et al. (1989) *Br. J. Pharmacol.* 97:1051-1058), involvement in signal transduction (Blay et al. (1989) *Biochem J.* 259:577-583; Creutz et al. (1987) *J. Biol Chem.* 262:1860-1868), calcium channel activities (Diaz-Munoz et al (1990) *J. Biol. Chem.* 265:15894-15899; Majima et al. (1990) *J. Immunol.* 145:1694-1699), exocytotic mechanisms (Ali et al. (1989) *Nature* 340:313-315), and blood anti-coagulant properties (Tait et al. (1989) *J. Biol. Chem.* 264:7944-7949; Funakoshi et al. (1987) *Biochem.* 26:5572-5578).

At least eight distinct proteins are now known to constitute this family of molecules in humans, characterized by a common core structure consisting of four repeats of a 70 amino-acid unit, which probably forms the calcium and phospholipid binding site (Schlaepfer et al. (1987) *J. Biol. Chem.* 262:6931-6937; Haigler et al. (1989) *TIBS* 14:48-51; Pepinsky et al. (1988) *J. Biol. Chem.* 263:10799-10811). However, questions concerning the significance of the differing N-terminal regions of the various lipocortins, the mechanism by which they exert their effects, and the physiological relevance of these proteins, remain unanswered.

The gene for human lipocortin-1 having a molecular weight of 37,000 daltons (37 kD) was the first to be cloned from the annexin family (Wallner et al. (1986) *Nature* 320:77-81), and its amino-acid sequence shares more than 50% homology with other members of the family (Pepinsky et al., ibid.). Inducibility of lipocortin-1 by glucocorticoids, and its inhibition of $PLA_2$ activity have been demonstrated (Flower, ibid.: Goulding, ibid.; Hirata et al. (1980) *Biochem.* 77:2533-2536; Rothhut et al. (1989) *Biochem. J.* 263:929-935; Browning et al. (1990) in *Cytokines and Lioocortins-1 in Inflammation and Differentiation* (Melli et al., eds.) Wiley Liss, New York), but the physiological relevance of these findings as well as the mechanism by which lipocortin-1 inhibits $PLA_2$ remain complex and unclear.

Recently it has been demonstrated that purified lipocortin-1 has an acute anti-inflammatory effect in the rat paw edema test (Cirino et al. (1989) *Proc. Natl. Acad. Sci. (USA)* 86:3428-3432), and mimics many anti-inflammatory effects of glucocorticoids including inhibition of neutrophil (polymorphonuclear cells, PMNs) superoxide generation (Maridonneau-Parini et al. (1989) *J. Clin. Invest.* 83:1936-1940), chemotaxis (Fradin et al. (1988) *Biochim. Biophys. Acta* 963:248-257), and production of eicosanoids, $PGE_2$ and $LTB_4$ (Glenney et al. (1988) *Biochem.* 27:2069-2076). A unifying characteristic of the diverse properties of lipocortin-1 is that its extracellular biological activities are dependent upon the presence, correct amino acid sequence and conformational orientation of the N-terminal domain (Browning et al., ibid.).

SUMMARY OF THE INVENTION

A new cellular receptor protein has been discovered on the surface of monocytes, neutrophils, and platelets that binds lipocortin-1. This lipocortin-1 binding molecule (LBM) appears to take part in the mechanism involving the inflammatory response of the body to infection and injury.

Based on this discovery, a number of diagnostic and therapeutic reagents have been developed which are useful in stimulating the inflammatory response, inhibiting the response, and/or predicting the capacity of the organism to respond to infection, injury, or autoimmune assault.

Accordingly, this invention provides a substantially pure lipocortin receptor protein which is derivable from the cell membranes of monocytes or neutrophils (herein collectively called "leukocytes", "phagocytes", or "PMNs"), from the cell membranes of platelets, or which can be produced by recombinant DNA techniques. Also provided are a nucleic acid encoding at least a portion of this protein, a replicable expression vector capable of expressing that nucleic acid in a transformed cell, a cell transformed with that nucleic acid, and a polyclonal or monoclonal antibody which is specific for the protein.

In one embodiment of the invention, polypeptide fragments of the LBM are disclosed. These LBM-related polypeptides include a portion of an LBM including at least the extracellular domain of the LBM exposed on the surface of monocytes and neutrophils. The term "portion" is used herein to encompass native or recombinant LBM proteins or partial proteins produced by biosynthetic or biochemical means. In the present invention, the LBM fragments, like the entire LBM, have the ability to bind lipocortin-1.

Other reagents encompassed by the invention include analogs, agonists, and antagonists of lipocortin-1 which bind the LBM, and analogs, agonists, and antagonists of the LBM which bind lipocortin-1.

Analogs of lipocortin-1 include those proteins or polypeptides having an amino acid sequence sufficiently duplicative of the sequence of lipocortin-1 such that they bind the LBM to the exclusion of lipocortin-1. Agonists of lipocortin-1 also bind the LBM, possibly to the exclusion of lipocortin-1. When the LBM is on the surface of a cell normally expressing this protein, such as a monocyte or neutrophil, the binding of a lipocortin analog does not alter or inhibit the normal inflammation-related activities of that cell, whereas the binding of an agonist may even enhance that response. On the other hand, the binding of antagonists to the LBM to the exclusion of lipocortin-1 inhibits, alters, or reduces the normal response of cells having an LBM to infection, injury, or autoimmune assault.

Analogs and agonists of the LBM include those proteins or polypeptides having an amino acid sequence sufficiently duplicative of the sequence of the native LBM such that they bind lipocortin-1. Antagonists of the LBM include soluble fragments of the LBM which bind lipocortin-1, thereby reducing the normal response of cells having an LBM to infection, injury or autoimmune assault.

In addition, various methods of determining the presence or amount of the LBM on a cell are provided. These methods include providing a binding molecule, such as an antibody, which binds the lipocortin-1 receptor protein, contacting the cell to be tested with the binding molecule, and determining the binding of the binding molecule to the cell as an indication of the presence or amount of receptors on the cell surface.

Other embodiments of the invention include methods of stimulating immune function in a subject and methods of assessing the responsiveness of a subject to glucocorticoid suppression of immune or inflammatory response.

Immunity can be stimulated by preparing a therapeutic formulation containing a compound which blocks receptor activity (a stimulator of immune cell function) and a physiologically acceptable vehicle, and treating the subject with the therapeutic formulation. The stimulator is a molecule selected from the group consisting of an anti-lipocortin-1 antibody, an anti-lipocortin-1 receptor protein antibody, a lipocortin-1 antagonist, and a soluble fragment of the lipocortin-1 receptor protein.

The responsiveness of a subject to glucocorticoid suppression of an immune or inflammatory response may be assessed by measuring the level of the lipocortin-1 receptor protein on a leukocyte from the subject, and then comparing the measured level to levels from normal subjects as an indication of responsiveness. In this method, results including a low level of lipocortin-1 receptor protein are indicative of responsiveness of the subject to glucocorticoid suppression.

BRIEF DESCRIPTION OF THE DRAWINGS

The foregoing and other objects of this invention, the various features thereof, as well as the invention itself, may be more fully understood from the following description, when read together with the accompanying drawings, in which:

FIG. 1 is a diagrammatic representation of the model for the role of lipocortin-1 in the inflammatory response.

FIG. 2 is a graphic representation of the binding of recombinant human lipocortin-1 to human leukocytes;

FIG. 3 is a histogram showing the calcium-dependence and specificity of lipocortin-1 binding to human leukocytes;

FIGS. 4A and 4B are histograms showing the binding of (a) maximum and (b) endogenous lipocortin-1 to leukocytes from healthy controls;

FIG. 5 is a photographic representation of an SDS-polyacrylamide gel of lipoprotein-1 binding protein immunoprecipitated with lipocortin-1 and antibody RPC5;

DETAILED DESCRIPTION

It has been discovered that lipocortin-1 binds a receptor molecule on the surface of leukocytes, thereby regulating the immune or inflammatory response to an infection or injury.

The model depicted in FIG. 1 describes the role of lipocortin-1, and perhaps other glucocorticoid induced molecules, in the inflammatory response. Following an acute inflammatory assault, stimulation of the hypothalamic-pituitary-adrenal axis results in the release of cortisol, which in turn results in the production of lipocortin-1 at discrete sites throughout the body. Neutrophils and monocytes trafficking to tissue sites then have to pass through regions of elevated lipocortin-1 concentration. At this point, the lipocortin-1 binding molecules are engaged with resultant down-regulation of migratory and/or pro-inflammatory activities of monocytes and neutrophils. At inflammatory sites, either leukocyte migration would occur before lipocortin-1 levels become elevated, and/or the presence of inflammatory mediators would counter balance the suppressive effects of lipocortin-1.

The LBM or fragments thereof can be purified from monocyte, neutrophil, or platelet membrane preparations by any of a number of known biochemical fractionation techniques, such as gel filtration, ion exchange chromatography, high pressure liquid chromatography or the like. The appropriate fraction from the gel or chromatography column can be identified by assaying aliquots from each fraction, for example, by a soluble receptor binding assay employing radiolabelled lipocortin-1. Alternatively, or as an additional purification step, affinity chromatography can be employed using a solid phase lipocortin-1 affinity column (e.g., lipocortin-1 bound to microbeads), or an antibody column (e.g., with monoclonal antibodies prepared as described above, bound to a solid support) to obtain purified LBM proteins or fragments thereof.

The proteins or fragments can then be analyzed to obtain the amino acid sequence (i.e., preferably about 10–35 amino acid residues) of the amino terminal portion of the LBM molecule. Samples of homogeneous LBM protein, as isolated above, can be analyzed for amino acid composition and sequence using an automated sequencer (Applied Biosystems, Beckman or equivalent protein sequencer) employing the Edman degradation or similar techniques (see generally Konigsberg et al. and Niall (1977) *The Proteins,* 3:1–178 and 279–238, respectively, herein incorporated by reference for further description of amino acid sequencing techniques).

The amino acid sequence from the purified protein can be used to construct a radiolabelled synthetic deoxyoligonucleotide probe complementary to a portion of the amino acid sequence. These probes comprise a group of nucleotide sequences which encode a small portion of the amino acid sequence of the LBM protein. Such "oligo probes" are constructed using conventional techniques from radiolabelled nucleotides by protecting one end of the first nucleotide with a blocking group and condensing this precursor with a nucleotide which is blocked at the other end. One of the blocking groups is then removed and the process of condensation, removal of one or the other blocking groups, and recondensation is repeated until an oligonucleotide of the desired length is obtained (see generally, Gail et al. (1977) *Nuc. Acids Res.* 4:1135-1158, herein incorporated by reference, for further details of oligonucleotide synthesis).

A cDNA library is constructed by extracting the cytoplasmic RNA from a neutrophil, monocyte, or any cell line known to express the LBM protein. mRNA may be separated from total cellular RNA using an oligo-dT-cellulose or poly U column.

For example, total RNA can be isolated from monocytes or neutrophils by solubilization in 4.0M guanidine hydrochloride, 20 mM sodium acetate, pH 5.0, followed by ultracentrifugation through a 5.7M cesium chloride cushion (see Aviv et al. (1982) *Proc. Natl. Acad. Sci.* (USA) 69:1408, herein incorporated by reference for further chromatography details). Poly A+ RNA is prepared by oligo-dT affinity column chromatography. In addition, this mRNA can be size fractionated by, for example, agarose gel electrophoresis. The fraction which includes the mRNA of interest may be identified by inducing transient protein expression in an in vitro system or a suitable host cell, such as frog oocyte cells. Transformed oocytes expressing LBM-related polypeptides can be detected by binding assays using radiolabelled lipocortin-1, or alternatively, by binding using radiolabelled antibodies reactive with the LBM protein or portions or analogs thereof.

The appropriate mRNA fraction selected is copied to single-stranded cDNA using reverse transcriptase, and the second cDNA strand is then synthesized by DNA polymerase I. The cloned, double-stranded cDNA is introduced into a plasmid vector which is then transfected into an appropriate bacterial host, such as *E. coli*. The entire collection of cDNA clones can be separated from each other by limiting dilution techniques to form a collection of bacterial colonies which comprise the cDNA library (see Sambrook et al. *Molecular Cloning, A Laboratory Manual* (2nd Ed.) pp. 188-246 (1982), herein incorporated by reference, for further details of mRNA extraction and cDNA cloning).

Portions of the individual bacterial colonies that comprise the cDNA library are then transferred onto filter paper and lysed. The filter is then washed to remove intracellular debris, and the DNA is fixed to the filter by baking. The immobilized DNA is then treated with the radiolabelled oligonucleotide probe, prepared as described above. If DNA complementary to the probe is present in a particular colony, the probe will hybridize to it, thus rendering it detectable by autoradiography.

The particular colony can then be further cultured and its DNA extracted therefrom to isolate the LBM gene. From this gene, the DNA sequence (and, consequently, the full corresponding amino acid sequence) can be determined, for example, by the Maxam-Gilbert sequencing technique or related procedures *Meth. Enzymol.* (1980) 65:479-559, herein incorporated by reference, for further details of DNA sequencing).

The plasmid containing the LBM gene or various portions thereof can be further transfected into other cell lines for expression or large scale production. Moreover, the gene can be modified to produce analog polypeptides or portions of the LBM that retain LBM epitopic features and binding activity. For example, the extracellular domain of the LBM can be produced from the gene sequence that encodes this fragment of the protein (see, *Principles of Gene Manipulation* (1981), herein incorporated by reference, for a further discussion of cloning vehicles and gene manipulation procedures).

Alternatively, the process of purifying the protein, sequencing it, and preparing oligonucleotide probes can be bypassed, and direct observations of expression substituted instead. In this approach, a cDNA library is established as before by extracting cytoplasmic RNA from LBM expressing cells and is used to form complementary DNA as discussed above. The cDNA library cloned into *E. coli* can then be incorporated into vectors with appropriate promoters (e.g., a Okyhama-Berg vector with an SV-40 promoter) and transfected in eucaryotic cells, such as African Green Monkey kidney cells (i.e., COS-7 cells), to express the LBM protein analog, or active fragment thereof. Specific binding with radiolabelled lipocortin-1, radiolabelled lipocortin-1 fragment, or radiolabelled monoclonal antibodies to an LBM epitope will permit the selection of functional transformants.

To identify the bacterial colony containing the cDNA encoding the LBM or LBM fragment, the bacteria are cloned and frozen. Pools of 10-20 bacterial colonies are then transfected into COS-7 cells, which are then assayed for LBM expression, either through lipocortin-1 binding or by antibody binding. Positive pools are re-assayed whereby each individual colony is transfected. After identification of the positive bacterial clones, the cDNA insert can be handled as described above.

Alternatively, if the concentration of mRNA transcribing the LBM protein is low in a given cell, the total genomic DNA can be transfected into mouse fibroblasts. Mouse cells which express the surface receptor and can be identified, e.g., by rosette reaction with antibody-coated red blood cells. These transfected mouse fibroblasts then be selected and used, according to steps described above, in constructing a cDNA library and isolating the gene of interest.

Polyclonal antibodies to the LBM, or fragments of the LBM can be generated by well known techniques including the immunization of a mammal such as a mouse, rabbit, or goat with an immunogen containing the LBM and then administering a booster injection several weeks later to insure the production of antisera reactive with LBM.

Monoclonal antibodies to the LBM protein, or active fragments of such antibodies, can be generated by applying generally known cell fusion techniques (see, e.g., Kohler et al. (1976) *Eur. J. Immunol.* 6:511-519; and Shulman et al. (1978) *Nature* 276:269-270, herein incorporated by reference) to obtain a hybridoma producing the antibody, by deriving a monoclonal antibody from the hybridoma, and (optionally) by subjecting the monoclonal antibody to proteolysis to obtain the active antibody fragments.

Briefly, the monoclonal antibodies are prepared by obtaining mammalian lymphocytes (preferably spleen cells), committing the lymphocytes to produce anti-LBM protein antibodies, fusing the so-committed lymphocytes with myeloma (or other immortal) cells to form hybrid cells, screening the hybridomas for lipocortin-1 receptor protein binding, and then culturing a selected hybrid cell colony in vivo or in vitro to yield anti-LBM antibodies which are identical in structure and specificity.

In particular, monoclonal antibodies to the LBM protein can be raised using an immunogen containing the LBM protein. For example, whole cells from a monocyte/neutrophil cell line may be employed. A partially purified fraction of a homogenate of an LBM-expressing cell line, such as a membrane fraction, can also be used as an immunogen. Alternatively, the immunogen may be a highly purified fraction of such a cell homogenate, or a biochemically synthesized or genetically engineered LBM protein, or active analogs or active fragments thereof.

This immunogen, emulsified or suspended in complete Freund's adjuvant, is injected into mice, rabbits, rats, goats, or other animals. After the initial injection, booster injections can be administered without adjuvant or emulsified in incomplete Freund's adjuvant. The animals so challenged commit a population of T lymphocytes to the production of antibodies to the LBM protein.

Serum samples from the immunized animal can be screened for the presence of anti-LBM polyclonal antibodies by an enzyme-linked immunoabsorbent assay ("ELISA") or the like for antibody reaction with the immunization agent. Animals that exhibit antibodies titers are sacrificed and their spleens homogenized. Alternatively, the spleen cells can be extracted and the antibody-secreting cells expanded in vitro by culturing with a nutrient medium. The spleen cells are then fused with myeloma (or other immortal) cells by the procedure of Kohler and Milstein (ibid.).

The hybridomas so produced (i.e., cloned by the limiting dilution procedure of Baker et al. (ibid.)) are screened to select a cell line producing antibodies which recognized the LBM proteins. Screening for reactivity with the LBM protein can be performed by standard immunoassay methods.

Large scale antibody production can be obtained from such anti-LBM antibody-producing cell lines by various techniques, including the induction of ascites tumors (e.g., after priming with pristane), followed by the purification of such antibodies from the ascites fluid by Protein A-Sepharose affinity chromatography. For a further description of general hybridoma production methods, see Oi and Herzenberg in *Selected Methods in Cellular Immunology* (Mishell and Shiigi, eds.) W. H. Freeman & Co. (1980); Scearce et al. (1983) *Meth. Enzymol.* 103:459–469; and U.S. Pat. No. 4,411,933 issued to Gillis on Oct. 25, 1986, herein incorporated by reference.

Human antibodies (i.e., those obtained from human-human or human-animal hybridoma) or chimeric antibodies can be used as well as animal antibodies. For descriptions of human hybridoma production techniques, see U.S. Pat. No. 4,451,570 issued to Royston et al. on May 29, 1984; U.S. Pat. No. 4,529,694 issued to Lazarus et al. on Jul. 16, 1985 and Zurawski et al. (1980) in *Monoclonal Antibodies* Plenum Press, New York), also incorporated by reference. Chimeric antibodies can be produced by standard techniques.

Active antibody fragments can be derived from the monoclonal antibodies disclosed herein by a number of techniques. For example, purified monoclonal antibodies can be cleaved with an enzyme such as pepsin, and then subjected to HPLC gel filtration. The appropriate fraction containing Fab can then be collected and concentrated by membrane filtration or the like. For further description of general techniques for the isolation of active fragments, see, e.g., Khaw et al. (1982) *J. Nucl. Med.* 23:1011–1019 (1982), herein incorporated by reference.

The antibodies and antibody fragments used herein can be labelled with enzymes, radioisotopes, or fluorescent compounds. For example, antibodies can be tagged with radioactive labels by a variety of techniques including the Baker et al. technique. The biologically active molecules can also be labelled with a radionucleotide via conjugation with the cyclic anhydride of diethylenetriamine penta-acetic acid (DTPA) or bromoacetyl aminobenzyl ethylamine diamine tetra-acidic acid (BABE) (see, e.g., Hnatowich et al. (1983) *Science* 220:613–615; and Meares et al. (1984) *Analyt. Biochem.* 142:68–78, incorporated by reference).

The antibodies of this invention can be used in various quantitative assays including enzyme immunoassays, radioimmunoassays, heterogeneous and homogeneous assays, enzyme linked immunosorbant assays ("ELISA"), and the like.

An exemplary assay for lipocortin-1 or for the LBM protein which employs the antibodies of the invention may be carried out as follows. Pure LBM protein, or a lipocortin-1 binding fragment or analog thereof, is fixed to a solid support such as polystyrene beads or plastic microtiter wells. Samples containing lipocortin-1 are incubated with the LBM protein or fragment, allowed to bind, and then washed to remove any unbound lipocortin-1. To detect the lipocortin-1, a developing reagent consisting of the anti-LBM monoclonal or polyclonal antibodies that have been radiolabelled can be used (see generally, Roitt (1980) *Essential Immunology*, Blackwell Press, pp. 137–171; and U.S. Pat. No. 4,376,110 issued to David et al. on Mar. 8, 1983, incorporated by reference, for further descriptions of immunoassay techniques).

A measurement of the number of LBMs on the surface of a cell may be determined by using a competitive [$^{125}$I]-lipocortin-1 binding assay. Monocyte/neutrophil cells are incubated in microfuge tubes overlayed over silicone oil/parrafin oil mixture as described by Robb et al. (*J. Exp. Med.* (1981) 154:1455–1474). Radiolabelled lipocortin-1 is added to each tube along with dilutions of control and immunized mouse sera, hybridoma supernatant, or monoclonal antibodies purified from hybridoma culture supernatant by precipitation with saturated ammonium sulfate. The tubes are incubated at 37° C., then centrifuged. The tips of the tubes containing the cell pellets are cut and counted using a solid scintillation counter as the "bound" fraction. The supernatants are counted as the "free" fraction. Results are expressed as percent "bound" in the absence of competitor.

The present invention also gives rise to a number of diagnostic and therapeutic agents useful in determining the presence or amount of LBM on the surface of a particular cell type, in suppressing an inflammatory response in a subject, and in stimulating immune function in a subject.

It has been determined that the level of LBM on the surface of monocytes and neutrophils of a subject reflects that subject's responsiveness to steroids such as cortisol and other glucocorticoids, and to lipocortin-1. Hence, assays measuring the number of LBMs on the cell surface are useful in showing a predisposition to diseases such as rheumatoid arthritis, where the LBM levels are abnormally low (see the Examples). Conversely, abnormally high LBM levels on leukocytes would probably result in an inadequate immune or inflammatory response, since this situation may lead to inhibiting responses required for immunity.

The amount or presence of LBM on the surface of a cell can be determined by a number of different assays. For example, a cell to be tested, such as a neutrophil, monocyte, platelet, or any cell genetically engineered to produce the LBM, is contacted with a molecule which binds the LBM. Useful LBM binding molecules include anti-LBM antibodies, or binding portions thereof, lipocortin-1, and analogs or agonists thereof which bind LBM. Binding can be quantitated by labeling the LBM binding molecule with, for example, a radioisotope, enzyme, or fluorescent molecule. Alternatively, binding can be determined with the use of a molecule that binding the anti-LBM antibody, such as Protein A or a second antibody such as an anti-immunoglobulin antibody. Binding of the LBM binding molecule to the cell is determined as indicative of the absence or presence and amount of LBMs on the cell surface.

Alternatively, the level of LBM on a cell may be determined by measuring the ability of the Fc receptor on the same cell to bind IgG, as this ability correlates directly with LBM interaction with lipocortin-1. This method may be integrated into a method of screening agents for agonistic activity against the lipocortin-1 receptor protein. In this method, a leukocyte bearing the lipocortin-1 receptor protein and bearing an Fc receptor for IgG, such as a monocyte or neutrophil, is contacted with the agent to be screened. The agent's ability to inhibit IgG binding to the Fc receptor is then determined. This ability is an indication of agonistic activity on the part of the agent, as the binding of IgG to the Fc receptor on a leukocyte is directly related to the binding of the lipocortin-1 receptor protein at the lipocortin-1 binding site.

The reagents of the invention may also be used for stimulating immune function in a subject. Immunity stimulation may be accomplished by providing a therapeutic formulation including a stimulator of immune cell function and a physiologically acceptable vehicle, and treating the subject with this formulation. The stimulator of immune cell function may be an anti-lipocortin-1 antibody, an anti-LBM antibody, a natural or engineered lipocortin-1 antagonist, or a soluble fragment of the LBM. The stimulators act to inhibit the binding of lipocortin-1 to its receptors on monocytes and neutrophils, thus not impeding the inflammatoryinducing mission of these cells. The therapeutic formulation may be administered at the site of infection or tumor, for example, by bolus injection. Alternatively, it may be injected systemically as an adjuvant with a useful immunogen such as a tumor cell marker.

Of course, antibodies to lipocortin-1 can be used to measure endogenous levels of lipocortin-1. This measurement could be used to quantify the in vivo bioactivity of glucocorticoids. It is therefore useful in monitoring patients receiving glucocorticoid therapy, and in assessing whether subjects with cancer will respond favorably to various biological response modifiers.

LBM agonists can be used in instances where suppressing immune function is desirable, for example, inducing tolerance in subjects afflicted with multiple sclerosis or rheumatoid arthritis, or for preventing graft rejection and graft-versus-host disease.

LBM-related agents may also be employed to influence platelet survival in a disease such as immune thrombocytopenia, as platelets have LBMs on their cell membranes.

Further uses of LBM agonists or lipocortin-1 itself include treatment of allergies and psoriasis. All autoantibody-mediated blood dyscrasis such as autoimmune hemolytic anemia, autoimmune neutropenia, ITP, etc., and to inhibit Fc receptor function sufficiently to reduce antibody or immune complex clearance rates.

Thus, by employing a combination of recombinant human lipocortin-1, specific monoclonal antibody, and fluoresceinated anti-mouse F(ab')$_2$ IgG, the number of lipocortin-1 molecules bound per cell has been estimated. Discrete, saturable binding, and absolutely consistent differential levels of binding of lipocortin-1 to monocytes, neutrophils and lymphocytes, reproduced in all eleven individuals examined, suggest that the molecule is not merely coating membrane phospholipid. The identification of lipocortin-1 binding proteins on human leukocytes provides new insights into the mechanism of extracellular lipocortin-1 effects on both inflammatory and immune processes.

Lipocortin-1 levels are low in serum and plasma ($<5$ ng/ml) as detected by sensitive ELISA (Goulding et al. (1990) *Lancet* 335:1416–1418), but the protein is present in large quantity in the lining layers of the rheumatoid synovium measured by immunohistological localization. Thus, the relative lack of lipocortin-1 binding sites on RA leukocytes would have fundamental implications for the lack of down-regulation of the inflammatory and immune responses which are so characteristic of this disease.

The invention is illustrated further by the following nonlimiting examples.

EXAMPLES 1. Subjects

Eleven healthy subjects (5 male; 6 female; age range 23–68 years), not receiving current medication and with no overt infections, were recruited for this study. Two groups of patients with chronic inflammatory disease were also studied including 8 patients with classical or definite rheumatoid arthritis (2 male; 6 female; age range 27–77 years), and 7 patients with ankylosing spondylitis were recruited (6 male; 1 female; age range 37–62). All patients were only receiving non-steroidal anti-inflammatory agents and had been on stable therapy for at least three months. No patients were receiving glucocorticoids or other disease-modifying antirheumatic drugs. 2. Cell Separation and Purification Mononuclear cells, neutrophils, and platelets were freshly isolated from peripheral blood of normal donors and patients after informed consent using a Ficoll-hypaque M-85 single step gradient (Ferrante et al. (1978) *J. Immunol. Meth.* 24:389–393). After washing with RPMI-1640 and PBS, cells were resuspended in Hepes-buffered RPMI-1640 + 0.02% $CaCl_2$ + 2 mg/ml BSA. In experiments to determine the sensitivity of lipocortin-1 binding to protease pre-treatment, cells at a concentration of $1 \times 10^6$/ml were incubated with a final concentration of 250 μg/ml trypsin for 40' at 37° C. with gentle rotation. Proteolysis was then quenched by a three fold dilution of the reaction mixture in RMPI 1640 containing 10% fetal bovine serum. The cells were subsequently washed three times in RPMI-1640 before being resuspended in Hepes-buffered RPMI-1640+0.02% $CaCl_2$+2 mg/ml BSA. 3. Preparation of Lipocortin-1

Recombinant human lipocortin-1 was produced in *Escherichia coli* (Wallner et al. (1986) *Nature* 320:77) and purified (>99%) by previously described methods (Pepinsky et al. (1986) *Nature* 321:81). The purified protein was dissolved in 25 nM Tris-HCl buffer pH 7.7 with between 0.1 and 5 mM EDTA and 0.1 mg/ml human serum albumin (essentially globulin free). Preparations contained less then 50 pg/ml endotoxin. *Escherichia coli* of the same strain were processed which lacked the lipocortin-1-containing plasmid. This material in the same Tris-HCl buffer pH 7.7 was used as a control 'sham' preparation. Alternatively, recombinant human lipocortin-1 was obtained from Biogen (Cambridge, Mass.).

4. Flow Cytometry

An indirect immunofluorescence assay was used in which the binding of recombinant human lipocortin-1 (Biogen, Cambridge, Mass.) was detected with a specific monoclonal antibody, mAb 1-B (Biogen, Cambridge, Mass.), which shows no apparent crossreactivity with other lipocortins (Pepinsky et al., ibid.).

Cells were incubated as a mixture (i.e., lymphocytes, monocytes, and neutrophils) with recombinant lipocortin-1 (total volume 60 µl) for 1 h at 4° C., then incubated with 20 µg/ml mAb 1-B for 1 h at 4° C. after washing with 200 µl PBS-BSA containing 0.02% $CaCl_2$ three times to remove free lipocortin-1. Cells were then washed three more times and incubated with fluorescein isothiocyanate (FITC) labeled-goat $(Fab)_2$ anti-mouse IgG (Caltag, Inc.) for 1 h at 4° C.

Monocytes, neutrophils and lymphocytes were examined individually by flow cytometry, gated by forward and 90° light scatter, and specific surface markers. Analysis was performed on either an Ortho 50H cytofluorograph or a FacStar Plus (Becton Dickenson) with 488 nm argon ion laser excitation. Cell-associated mean fluorescence intensity was converted to FITC equivalent second antibody molecules bound per cell according to a calibration curve using standard fluorescence beads (Flow Cytometry Standards Corp., Research Triangle Park, N.C.; Petroni et al. (1988) *J. Immunol.* 140:3467–3472).

5. Radioimmunoprecipitation

To test the hypothesis that lipocortin-1 is binding to a specific protein or proteins on the cell surface, monocytes/neutrophils from normal donors were subjected to surface iodination and immunoprecipitation with recombinant lipocortin-1 and mAb 1-B as follows. Monocytes/neutrophils were freshly isolated from monocyte/neutrophil-enriched leukopheresis packs using Ficoll-hypaque gradient separation and cold aggregation (Ando et al. (1989) *J. Biol. Chem.* 264:6948–6955). After overnight culture in RPMI-1640+10% fetal bovine serum (FBS), cells were labeled with $^{125}I$ using the lactoperoxidase method of Manjunath et al. (*J. Immunol.* (1986) 136:2271), and lysed with PBS containing 0.5% NP-40, 0.02% $CaCl_2$, 0.02% $MgCl_2$, and a cocktail of proteinase inhibitors as previously described by Laemmli (*Nature* (1970) 227:680–685). After preclearing with protein A-sepharose three times, or anti-$PLA_2$ following protein A-sepharose three times, lysates were mixed with recombinant human lipocortin-1 for 1 h. mAb 1-B was then added. Samples were rotated overnight at 4° C., then mixed with protein A-sepharose for 4 h. After washing with lysis buffer six times, samples were eluted in 2× for 3 minutes or eluted in 50 µl of 10 mM EGTA in sample buffer plus 8% β-mercaptoethanol by boiling PBS, then added to an equal volume of 2× sample buffer plus 8% β-mercaptoethanol.

6. SDS-Polyacrylamide Gel Electrophoresis

Samples were analyzed by 10% reducing SDS-PAGE essentially as described by Morganelli et al. (*J. Immunol.* (1988) 140:2296–2304), herein incorporated by reference.

7. Monomeric IgG Binding

Human 7S IgG1, from the plasma of a patient with multiple myeloma, was purified by ion-exchange and affinity chromatography. The isolated IgG was subsequently radiolabelled with $^{125}$Iodine (Amersham Corp., Arlington Heights, Ill.) using 1,3,4,6-tetrachloro-3,6-diphenylglycoluril (Iodogen; Pierce Chemical Co., Rockford, Ill.) Following separation of bound from unbound $^{125}I$ by filtration over a P6-DG column (Bio-Rad Laboratories, Richmond, Calif.), $^{125}I$-IgG was reacted with purified human monocytes obtained from leukophoresis of healthy subjects described by Shen et al. (*Clin. Exp. Immunol.* (1986) 65:387). The affinity constant for IgG binding and number of binding sites per cell were estimated according to the method of Scatchard (Girard et al. (1987) *J. Immunol.* 138:3235; Scatchard (1949) *Ann. NY Acad. Sci.* 51:660).

8. Results

Figure 2:
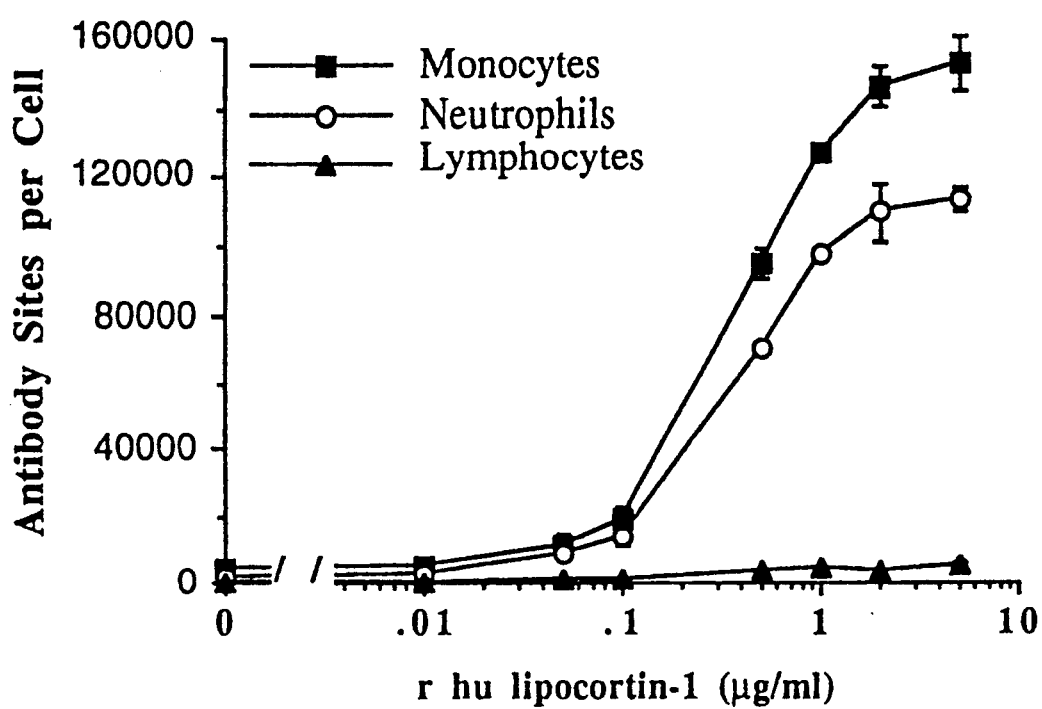

Saturable binding sites for lipocortin-1 were found on peripheral blood leukocytes from healthy donors. When cells were incubated for 30 minutes with increasing amounts of human recombinant lipocortin-1 at 4° C., dose-dependent lipocortin-1 binding to human leukocytes was detected with specific mAb 1-B followed by FITC conjugated F(ab')$_2$ fragment of anti-mouse IgG. The results are shown in FIG. 2. Differentially higher binding was observed to monocytes>neutrophils>lymphocytes. Representative values shown in this figure are for one donor. The results are expressed as mean second antibody equivalent binding sites per cell±SD.

Significantly greater binding of lipocortin-1 to monocytes (average=80,000 sites/cell) than to neutrophils (average=30,000 sites/cell) was found in each of eleven donors tested, whereas negligible binding of lipocortin-1 to lymphocytes was observed. The binding of lipocortin-1 to both monocytes and neutrophils at 4° C. reached half-saturation at 0.5 µg/ml, and was maximum at 2 µg/ml. The time course of lipocortin-1 binding was extremely rapid, with half maximal binding occurring within 3 minutes. Maximal binding could be achieved within 1 hour.

Thus, by employing a combination of recombinant human lipocortin-1, specific monoclonal antibody, and fluoresceinated anti-mouse F(ab')$_2$ IgG, the number of lipocortin-1 molecules bound per cell has been estimated. Discrete, saturable binding, and absolutely consistent differential levels of binding of lipocortin-1 to monocytes, neutrophils, and lymphocytes, reproduced in all eleven individuals examined, suggest that the molecule is not merely coating membrane phospholipid. The identification of lipocortin-1 binding proteins on human leukocytes provides new insights into the mechanism of extracellular lipocortin-1 effects on both inflammatory and immune processes.

The calcium-dependence and specificity of lipocortin-1 binding to human leukocytes is shown in FIG. 3. Cells were incubated with 2 µg/ml human recombinant lipocortin-1 at 4° C. for 30 minutes in the presence or absence of calcium ions, 10 mM EDTA or a neutralizing anti-lipocortin-1 antibody (1-A). The results are expressed as mean second antibody equivalent binding sites per cell±SD. The binding of lipocortin-1 was abolished when cells were incubated with lipocortin-1 in the presence of EDTA, or allowed to bind lipocortin-1 in the presence of calcium, but then washed with calcium-free PBS.

FIG. 3 also demonstrates that monoclonal Ab 1-A, which neutralizes the anti-$PLA_2$ activity of lipocortin-1, also reduced the binding of lipocortin-1 to monocytes and neutrophils by 50–70%.

In addition, pre-incubation of monocytes/neutrophils with 250 μg/ml trypsin resulted in an 81% decrease in binding of mAb 1-B, another antibody specific for lipocortin-1. These results are summarized Table 1, in which the results are expressed in FITC-equivalent second antibody binding sites per cell±SD.

TABLE 1

| Treatment (mAb) | Control | +250 μg Trypsin |
|---|---|---|
| Lipocortin/1-B | 44700 ± 4900 | 8000 ± 700 |
| PM81 (CD15) | 27800 ± 3600 | 41400 ± 1100 |
| Mac 2.48 | 5000 ± 700 | 1400 ± 300 |

Expression of the CD15 surface antigen recognized by mAb Pm81, used as a negative control, was resistant to trypsinization. Binding of a positive control mAb Mac 2.48 to a 150 kD trypsin-sensitive antigen (Morganelli et al. (1988) *J. Immunol.* 140:2296–2304) showed a 70% reduction with trypsin treatment.

The finding that recombinant human lipocortin-1 binds to human monocytes and neutrophils (but not to admixed lymphocytes) in a dose-dependent, calcium-dependent and trypsin-sensitive fashion, suggests that the molecule is binding to a specific protein site on human monocytes and neutrophils and not merely to membrane phospholipid.

Figure 4A:
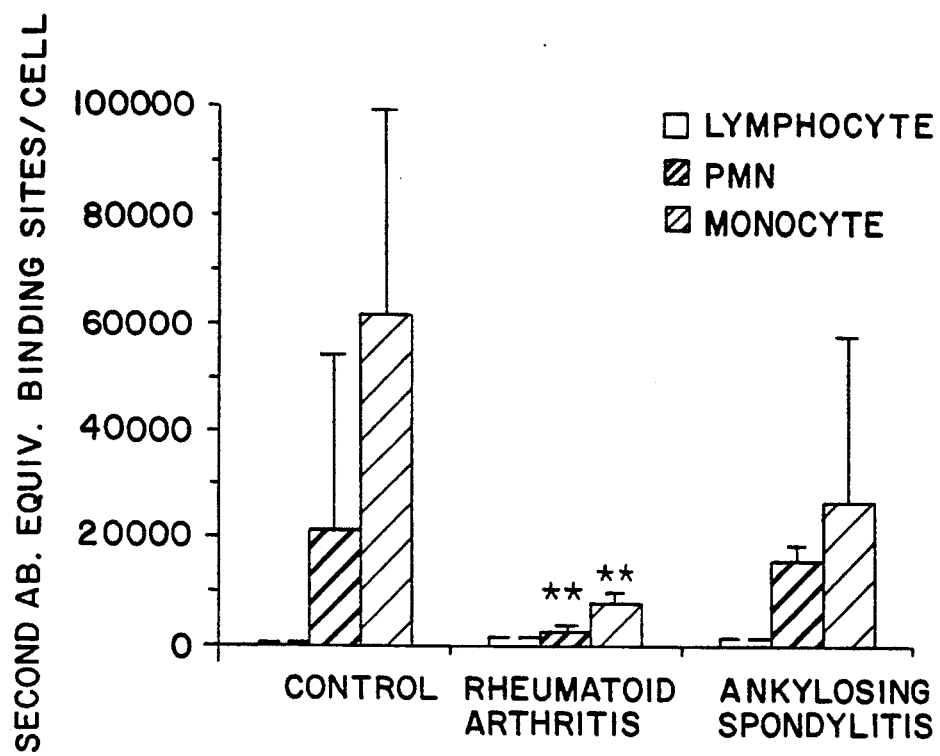

A comparison of exogenous lipocortin-1 binding to peripheral blood leukocytes isolated from healthy donors and rheumatoid arthritis patients is depicted in FIG. 4A. Cells were incubated with 2 μg/ml human recombinant lipocortin-1 at 4° C. for 30 minutes. The bars represent median FITC-equivalent second antibody binding sites per cell. The rheumatoid arthritis group had significantly lower binding than the control ankylosing spondylitis groups (p<0.01). The differential binding profile: monocytes>neutrophils>lymphocytes, was maintained in both inflammatory groups, but patients with rheumatoid arthritis exhibited a 90% reduction in lipocortin-1 binding to monocytes and neutrophils (p<0.01; Mann-Whitney U-test). Binding in the ankylosing spondylitis group was also reduced, but this did not reach statistical significance due to a wide interquartile range of binding.

Figure 4B:
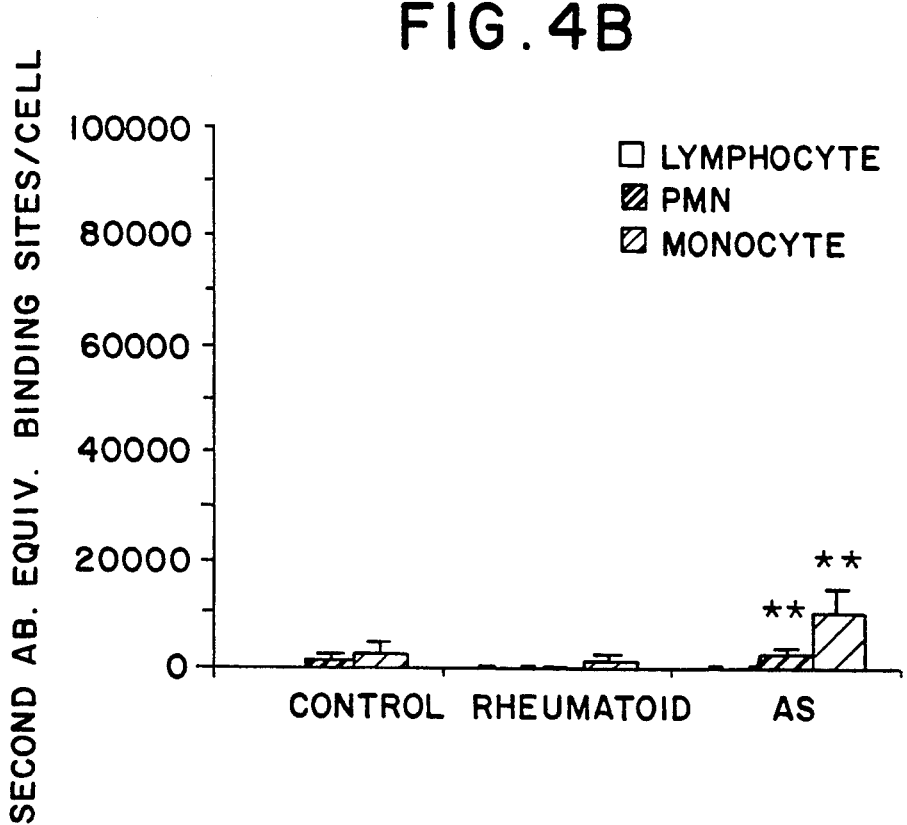

To obtain information about the amount of endogenous lipocortin-1 on the surface of cells when they are freshly isolated from peripheral blood, cells were probed with mAb 1-B alone, without prior addition of a saturating dose of exogenous lipocortin-1. FIG. 4B demonstrates that both controls and rheumatoid arthritis patients would appear to have low endogenous binding of lipocortin-1. In this study, cells were incubated with 2 μg/ml human recombinant lipocortin-1 at 4° C. for 30 minutes. The bars represent median FITC-equivalent second antibody bindin sites per cell. The ankylosing spondylitis group had significantly higher binding than the control and rheumatoid arthritis groups (p<0.01).

However, monocytes and neutrophils from the ankylosing spondylitis group expressed significantly higher amounts of bound endogenous lipocortin-1 (p<0.01 over control and rheumatoid arthritis groups, Mann-Whitney U-test). No significant differences in either saturable or endogenous lipocortin-1 binding on monocytes or neutrophils were seen between sexes, nor was there any correlation with age.

Figure 5:
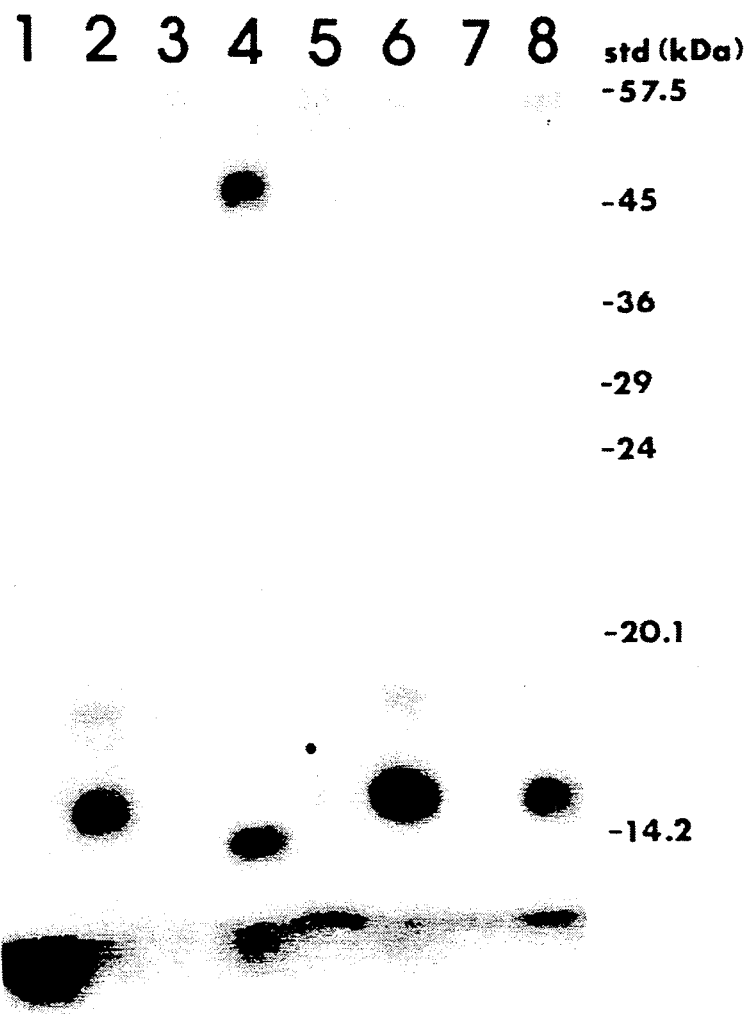

FIG. 5 shows the analysis of lipocortin-1 binding proteins that have been immunoprecipitated (as described above) and subjected to SDS-PAGE. Lane 1 shows immunoprecipitation with lipocortin-1 and an irrelevant monoclonal antibody RPC5. Lane 2 shows lipocortin-1 and mAb 1-B. Lane 3 shows mAb 1-B alone. Lane 4 shows mAb w6/32 anti-class I MHC antigen. Lane 5 shows the solid phase bead fraction after lipocortin-1 and mAb 1-B binding and elution with EGTA. Lane 6 shows lipocortin-1 and mAb 1-B after three fold preclearing with anti-$PLA_2$ antibody. Lane 7 shows anti-$PLA_2$ antibody. Lane 8 shows the supernatant fraction after lipocortin-1 and mAb 1-B binding and elution with EGTA.

This analysis demonstrates that recombinant lipocortin-1, in conjunction with mAb 1-B, immunoprecipitated two molecules with molecular weights of 15 kD, and 18 kD, respectively (lane 2). Monoclonal Ab 1-B alone did not precipitate any radiolabelled molecules (lane 3), indicating that the 15 kD and 18 kD molecules specifically bound to exogenous lipocortin-1, and were not proteolytic fragments of endogenous lipocortin-1, which would also be recognized by mAb 1-B. After washing immunoprecipitate-bound protein A-sepharose with PBS containing EGTA (lane 8), these two molecules were found in the supernatant, whereas the recombinant lipocortin-1 and mAb 1-B were still in the sepharose fraction (lane 5). Analysis of the same samples on 5–12% gradient SDS-PAGE did not show any radiolabelled molecules above molecular weight of 66 kD.

These data indicate that the 15 kD and 18 kD proteins bound to recombinant lipocortin-1 in a calcium-dependent fashion.

Since lipocortins-1 have been shown to inhibit the activity of $PLA_2$ (14 kD molecular weight), the 15 kD molecule brought down by lipocortin-1 was examined to determine whether it was $PLA_2$. No [$^{125}$I]-labelled molecules were detected by SDS-PAGE after immunoprecipitation using a polyclonal Ab to human platelet $PLA_2$, and preclearing of lysate with anti-$PLA_2$ antibody did not decrease the radioactive density of the 15 kD and 18 kD bands, suggesting that these two molecules are not related to platelet-derived $PLA_2$.

The effect of lipocortin-1 on expression and affinity of Fc gamma receptors (FcγR) on human monocytes was examined by measuring the binding of monoclonal antibodies directed against three defined types of FcγRs after short-term preincubation of cells with human recombinant lipocortin-1. The results are shown below in TABLE 2.

TABLE 2

| | CONTROL | | LIPOCORTIN-1 | |
|---|---|---|---|---|
| Expt. # | sites/cell $10^8 \times K_a (M^{-1})$ | FcγR | sites/cell $10^8 \times K_a (M^{-1})$ | FcγR |
| 1 | 1.8 | 20478 | 2.1 | 6795 |
| 2 | 1.9 | 31512 | 1.8 | 11069 |
| 3 | 15.0 | 15520 | 17.0 | 9458 |
| 4 | 11.0 | 17670 | 7.6 | 13467 |

In a series of 4 experiments, the mean $K_a$ value in the absence of lipocortin-1 was $7.4 \times 10^8$M, compared to $7.1 \times 10^8$M when cells were incubated with lipocortin-1. Preincubation with 395 nM lipocortin-1 had no effect on affinity constant of [$^{125}$I]-IgG surface binding to FcγR Type I. Maximal inhibition of binding of radioiodinated human IgG1 to purified human monocytes occurred when 15 μg lipocortin-1 per million cells (395 nM) was used (p<0.01). The number of IgG1 binding sites per cell was reduced 30 to 50% by 2 hour treatment with lipocortin-1, but there was no significant decrease in the affinity of IgG1 binding on the number of binding sites for monoclonal antibodies which recognize the three known types of FcγR. Similar observations were made for peripheral blood neutrophils.

These results suggests that lipocortin-1 binding to the LBM specifically interferes with the binding site for FcγRI.

EQUIVALENTS

Those skilled in the art will recognize, or be able to ascertain using no more than routine experimentation, numerous equivalents to the specific procedures described herein. Such equivalents are considered to be within the scope of this invention, and are covered by the following claims.

I claim:

1. A purified and isolated human lipocortin-1 binding molecule comprising a lipocortin-1 receptor protein which specifically binds lipocortin-1 in the presence of calcium, which is derived from the cell membrane of monocytes, which is essentially free of all other cell membrane proteins, and which has a molecular weight of about 15,000 daltons as determined by sodium dodecyl sulfate-polyacrylamide gel electrophoresis under reducing conditions.

2. The protein of claim 1 wherein the protein provides about 80,000 lipocortin-1 binding sites per monocyte at 4° C.

3. A purified and isolated human lipocortin-1 binding molecule comprising a lipocortin-1 receptor protein which specifically binds lipocortin-1 in the presence of calcium, which is derived from the cell membrane of monocytes, which is essentially free of all other cell membrane proteins, and which has a molecular weight of about 18,000 daltons as determined by sodium dodecyl sulfate polyacrylamide gel electrophoresis under reducing conditions.

4. The protein of claim 3 wherein the protein provides about 80,000 binding sites per monocyte at 4° C.

* * * * *